United States Patent [19]

Samour et al.

[11] 4,046,894

[45] Sept. 6, 1977

[54] CERTAIN BARBITURIC ACID DERIVATIVES USED AS ANTICONVULSANT AGENTS

[75] Inventors: Carlos M. Samour, Wellesley, Mass.; Julius A. Vida, Greenwich, Conn.

[73] Assignee: Bristol-Myers Company, New York, N.Y.

[21] Appl. No.: 125,813

[22] Filed: Mar. 18, 1971

Related U.S. Application Data

[60] Division of Ser. No. 888,943, Dec. 29, 1969, which is a continuation-in-part of Ser. No. 749,972, Aug. 5, 1968, abandoned.

[51] Int. Cl.$^2$ .......................................... A61K 31/515
[52] U.S. Cl. ...................................... 424/254; 260/257
[58] Field of Search ......................... 424/254; 260/257

[56] References Cited

U.S. PATENT DOCUMENTS

| | | | |
|---|---|---|---|
| 2,344,459 | 3/1944 | Henze | 424/254 X |
| 3,341,512 | 9/1967 | Wegmuller et al. | 260/257 |
| 3,663,699 | 5/1972 | Reinhard et al. | 424/254 |

OTHER PUBLICATIONS

Henze et al., Contributions for the Dept. of Chemistry, University of Texas, Aug, 1941.
War Dept. Army Medical Library Microfilm No. 1720, I. G. Farbenindustry, 1946.
Wilson & Grisvold — Textbook of Organic Medicinal & Pharmaceutical Chemistry 4th ed., 1962, pp. 336–340 & 363–366.
Remington's Pharmaceutical Sciences 13 ed., 1965, pp. 1144–1151.
Doran, Medicinal Chemistry vol. IV, John Wiley & Sons Inc., 1959, p. 187.

*Primary Examiner*—Leonard Schenkman
*Attorney, Agent, or Firm*—Irving Holtzman; Morton S. Simon; David J. Mugford

[57] ABSTRACT

Various derivatives of barbituric acid and of diphenylhydantoin are described in which alkoxymethyl or benzyloxymethyl groups are attached to the nitrogen atoms of the rings. Therapeutic compositions containing these compounds and their use as anticonvulsant agents are described.

5 Claims, No Drawings

CERTAIN BARBITURIC ACID DERIVATIVES USED AS ANTICONVULSANT AGENTS

This application is a division of copending application Ser. No. 888,943, filed Dec. 29, 1969, now pending which in turn is a continuation in part of application Ser. No. 749,972, filed Aug. 5, 1968, now abandoned.

This invention relates to selected substituted barbituric acids and hydantoins, to the use thereof as anticonvulsant agents for treating convulsions and seizures in warm-blooded animals, and to therapeutic compositions containing these compounds. More particularly, this invention relates to 1,3-dialkoxy (or dibenzyloxy)methyl-5,5-disubstituted barbituric acids having the formula

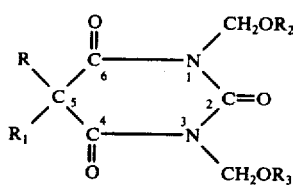

wherein R and $R_1$ are phenyl and ethyl respectively, or R and $R_1$ are individually alkyl or alkenyl each having 2 to 5 carbon atoms or cycloalkenyl having 5 to 7 carbon atoms, and wherein $R_2$ and $R_3$ are individually alkyl having 1 to 12 carbon atoms or benzyl; and to 3-alkoxymethyl-5,5-diphenylhydantoin or 1,3-dialkoxymethyl-5,5-diphenylhydantoin or 3-benzyloxymethyl-5,5-diphenylhydantoin.

Phenobarbital and diphenylhydantoin have both long been known to be useful as anticonvulsant agents in warm-blooded animals, having been employed in the treatment of epilepsy; however, phenobarbital suffers from the disadvantage that it exhibits hypnotic activity as well as anticonvulsant activity, while diphenylhydantoin has the disadvantage that although not hypnotic, it does have a multiplicity of undesirable side effects, for example, hypertrophic gingivitis, megaloblastic anemia, toxic psychoses, and hirsutism. It has now been found that N-lower alkoxymethyl phenobarbital and N-lower alkoxymethyl diphenylhydantoin compounds are effective anticonvulsants which possess unexpected advantages from the pharmacological standpoint over their respective parent compounds.

Although it has been reported in Doran, Medicinal Chemistry, New York 1959, Volume IV John Wiley & Sons, Inc. page 187 (War Department Army Medical Library, Microfilm No. 1720, I.G. Farbenindustrie Plant, Elberfeld, Germany) that a material identified by the structural formula of N,N'-dimethoxymethyl phenobarbital has been tested as a hypnotic and found to be without effect, there has been no indication that it has any useful therapeutic effect and no suggestion as to how to make it or what its properties are.

The compounds of the present invention are effective anticonvulsant agents for convulsions and seizures in warm-blooded animals and are free from hypnotic activity as hereinafter described. The compounds in which the alkoxy groups are methoxy or ethoxy are preferred; N,N'-dimethoxymethyl phenobarbital, and 3-methoxymethyl diphenylhydantoin are particularly preferred.

The compounds may be made by reacting an appropriate (e.g. alkali metal salt) barbiturate, such as phenobarbital sodium, or diphenylhydantoin sodium, with chloromethyl or other halomethyl alkyl or benzyl ether in a suitable diluent such as dimethyl formamide, dimethyl sulfoxide, dimethyl acetamide, hexamethylphosphoramide, and the like over a wide range of temperatures, conveniently from about −10° C. up to the boiling point of the diluent. The desired products are obtained in high yield and in an excellent state of purity; they can conveniently be isolated by conventional techniques such as extraction, distillation, filtration, preparative chromatography, etc.

Illustrative substituted barbituric acids which are employed in salt form to prepare compounds of the present invention include the following commercially available compounds: barbital, phenobarbital, probarbital, aprobarbital, amobarbital, allobarbital, vinbarbital, pentobarbital, cyclobarbital, 5-allyl-5-(2-cyclopentenyl)barbituric acid, 5-ethyl-5-cycloheptenyl barbituric acid, etc. Diphenylhydantoin sodium may also be used.

Among the halomethyl alkyl or benzyl ethers suitable for use in the preparation of the compounds of the present invention are chloromethyl methyl ether, chloromethyl ethyl ether, chloromethyl butyl ether, chloromethyl n-dodecyl ether, chloromethyl benzyl ether, and the like.

The compounds of the invention can be formulated with conventional physiologically acceptable vehicles and carriers to make syrups, isotonic solutions, tablets and other dosage forms. Toxicity and effectiveness of the compounds are such that each dosage unit can contain from 5 to 500 mg of active material. However in view of the high anticonvulsant activity of these compounds, dosage units containing from 5 to 200 mg of the compound are preferred.

The procedures employed for demonstrating efficacy of the compounds as set forth in the following examples were as follows.

All tests, with the exceptions noted, were conducted on adult albino male mice (Charles River strain); the dosage consisted of the active agent suspended in 10% aqueous acacia and was administered orally unless otherwise indicated.

Acute oral toxicity and acute intraperitoneal toxicity were determined in the conventional manner. The results were expressed as $LD_{50}$, the dose required to produce death in 50% of the animals treated, determined graphically, with the 95% limits shown in parentheses.

The dosage required to produce a neurological deficit was determined by the method of Swinyard et al., J. Pharmacol. Exptl. Therap. 106, 319 (1952) except that one additional test was employed: the ability of the animal to remain for at least one minute on a "rotorod," a horizontal rod rotated at 6 r.p.m. The results were expressed as $TD_{50}$, the dose required to produce the effect, determined graphically, with 95% limits.

Anticonvulsant effectiveness of each agent against maximal electroshock was determined at the time of peak effect. The time of peak anticonvulsant activity was determined by administering dosages of various sizes to a group of animals and administering a maximal electroshock to the animals at intervals thereafter by supplying 60 ma. current through a corneal electrode for 0.2 second. Protection was indicated if the animal failed to show the tonic extensor component of the maximal electroshock seizure pattern in unprotected animals. The time of peak effect thus determined was used for all subsequent tests of anticonvulsant activity on the same active agent.

Anticonvulsant effectiveness was determined against a convulsive dose of Metrazol (106.25 mg/kg) injected subcutaneously; the criterion for effectiveness was failure to show clonic convulsive seizures. Anticonvulsant activity was determined against a lethal dose of strychnine sulfate (1.5 mg/kg) injected subcutaneously; the criterion was failure to die, even though seizures appeared.

Hypnotic activity or depression of the central nervous system as indicated by loss of the righting reflex (onset of sleep) was not exhibited by any dosage of any of the compounds of the present invention less than a lethal dose. Phenobarbital itself, on the other hand, did exhibit hypnotic activity using the foregoing criterion.

The following examples will serve to illustrate the practice of this invention.

EXAMPLE 1

In a 1000 ml flask equipped with a stirrer and condenser, 136.4 g. (0.536 mole) of phenobarbital sodium powder was suspended in 500 ml of dimethylformamide. The flask was placed in an ice bath. To the cold suspension was added 100 g. (1.25 mole) of chloromethyl methyl ether over a period of one hour. The resulting suspension was stirred at room temperature for twenty hours, then poured into 2000 ml of ice water and the resulting suspension was stirred for two hours. The crude product was removed by filtration, and washed three times with 100 ml of distilled water, then dissolved in about 500 ml of hot ethanol. To the boiling solution 1 g. of activated carbon was added and the boiling solution was filtered through a Buchner funnel which contained a 1 cm. pressed layer of finely-divided diatomaceous silica. The cake was washed three times with 25 ml of ethanol and the hot solution together with the washings was allowed to cool to room temperature. The resulting crystals were filtered, washed with ethanol, and dried in a vacuum desiccator. There was obtained 58 g. of N,N'-dimethoxymethyl phenobarbital (also known as 1,3-dimethoxymethyl-5-ethyl-5-phenyl barbituric acid), melting point 115°–117° C.

Pharmacological testing of this compound gave the following results:

|  | Dosage,mg/kg |
|---|---|
| Acute Toxicity |  |
| $LD_{50}$ (oral) | 470 (376–588) |
| $LD_{50}$ (intraperitoneal) | 490 (408–588) |
| Neurological Deficit |  |
| $TD_{50}$ | 47 (33–66) |
| Anticonvulsant Activity |  |
| Maximal electroshock, $ED_{50}$ | 13.5 (8–23) |
| Metrazol, $ED_{50}$ | 47 (29–75) |
| Strychnine, $ED_{50}$ | 200 (125–320) |
| Time of peak activity | 2 hours |

Repeated daily dosage of the same animals for four days showed no significant change in the $ED_{50}$ to protect against maximal electroshock. The duration of the anticonvulsant effect against maximal electroshock was compared with that of phenobarbital sodium at a dosage level of 0.1 millimole/kg of each. The compound of this example protected only after two hours, but protection continued at about the same level for more than eight hours. Phenobarbital provided protection in less than 0.5 hour, but protection began to decrease after four hours and was nearly gone by eight hours.

Anticonvulsant activity of the compound against maximal electroshock was also measured in the rat (Sprague Dawley Strain); the $ED_{50}$ was found to be 6.6 (4.2–10.4).

EXAMPLE 2

5,5-Diphenylhydantoin sodium (27.5 g., 0.1 mole) was suspended in 250 ml of dimethylformamide. To the suspension was added over a period of 30 minutes 8.8 g. (8.25 ml) of chloromethyl methyl ether. The resulting suspension was stirred at room temperature overnight, then poured into 1 liter of ice water. A solid material precipitated. The suspension was stirred for one hour and the solid was removed by filtration, washed on the filter three times with 100 ml of water, and the wet cake was dissolved in 125 ml of ethanol with heating. To the boiling solution 1 g. of activated carbon was added and the boiling solution was filtered through a Buchner funnel containing a 1 cm pressed layer of finely-divided diatomaceous silica. The cake was washed three times with 15 ml of ethanol and the hot ethanol solution together with the washings was diluted with 100 ml of hot water, then allowed to cool to room temperature. The crystals which appeared were filtered and washed three times on the filter with 25 ml of 50% aqueous ethanol, then dried in a vacuum desiccator. There was obtained 20 g. of 3-methoxymethyl-5,5-diphenylhydantoin; m.p. 127°–128° (yield 67%). Pharmacological testing of this compound showed it to have $LD_{50}$ of approximately 500 mg/kg. It exhibited anticonvulsant activity (maximal electroshock) within less than 0.5 hour after ingestion, and the activity lasted for more than 2 hours; the $ED_{50}$ was less than 25 mg/kg.

EXAMPLE 3

Powdered phenobarbital sodium (25 g.) was suspended in 250 ml of dimethylformamide. With vigorous stirring 15.6 g of chloromethyl benzyl-ether was added to the suspension at room temperature. The reaction mixture was stirred overnight at room temperature. The suspension was then poured into 500 g of ice cold water, the mixture was stirred for one hour and the solid removed by filtration. The crude product was dissolved in about 150 ml boiling ethanol; to the boiling solution 0.5 gram of activated carbon was added, and the boiling solution was filtered through a Buchner funnel which contained a compacted layer of finely-divided diatomaceous silica. The cake was washed three times with 10 ml of ethanol and the hot solution together with the washings was allowed to cool to room temperature. The resulting crystals were filtered and recrystallized from 100 ml of ethanol in the same manner as described for the first crystallization. There was obtained 5.27 g of N,N'-dibenzyloxymethyl phenobarbital (also known as 1,3-dibenzyloxymethyl-5-ethyl-5-phenyl barbituric acid), m.p. 74°–75°.

EXAMPLE 4

Powdered phenobarbital sodium (25 g.) was suspended in 350 ml of dimethylformamide. With vigorous stirring 15 g of chloromethyl-(n)-butyl-ether was added to the suspension at room temperature. The suspension was stirred overnight at room temperature. The reaction mixture was then poured into 1 kg of ice cold water, the mixture was stirred for one hour, and the solid removed by filtration. The crude product was dissolved in hot ethanol (100 ml), 1 g of activated carbon was added and the boiling solution was filtered through a Buchner funnel which contained a compacted layer of finely-divided diatomaceous silica. The cake was washed three times with 10 ml of ethanol and the hot solution together with the washings was allowed to cool to room temperature. The resulting crystals were filtered and recrystallized two more times from 100 ml of ethanol in the same manner as described for the first crystallization. There was obtained 12.3 g of N,N'-di-(n)-butoxymethyl phenobarbital (also known as 1,3-di-(n)-butoxymethyl-5-ethyl-5-phenyl barbituric acid), m.p. 71°–72° C. When tested as described above the compound exhibited anticonvulsant activity against maximal electroshock, the $ED_{50}$ being less than 100 mg/kg.; and an $LD_{50}$ (oral) greater than 500 mg/kg.

EXAMPLE 5

Phenobarbital sodium (25 g) was dissolved in 250 ml of dimethylformamide at 120° C. The solution was cooled to 60° and at this temperature 25 g of chloromethylethylether was added with good stirring. The reaction mixture was allowed to cool to room temperature and stirred for 20 hours, then poured into 500 g of ice water, stirred for one hour, and the solid product was removed by filtration. The solid material was dissolved in 150 ml of boiling ethanol, 1 g of activated carbon was added and the boiling solution was filtered through a Buchner funnel which contained a compacted layer of finely-divided diatomaceous silica. The cake was washed three times with 10 ml of ethanol and to the hot solution together with the washings there was added 50 ml of hot water and the solution was allowed to cool to room temperature. The resulting crystals were filtered and recrystallized two more times in the same manner as described for the first crystallization. There was obtained 6.5 g of N,N'-diethoxymethyl phenobarbital (also known as 1,3-diethoxymethyl-5-ethyl-5-phenyl barbituric acid), m.p. 65°. When tested as described above, the compound exhibited anticonvulsant activity against maximal electroshock, the time of peak activity being 1½ hours and the $ED_{50}$ being less than 25 mg/kg.

EXAMPLE 6

5,5-Diphenylhydantoin sodium (27.5 g) was suspended in 250 ml of dimethylformamide at 100° C. The suspension was cooled to 50° C. with good stirring. At this temperature 16 g of chloromethyl-(n)-butylether was added and the suspension was stirred for three hours while allowing the temperature to drop to 20° C. The reaction mixture was then poured into 1 liter of ice cold water and stirred for one hour. The resulting solid product was removed by filtration and dissolved in 150 ml of hot ethanol; 1 g of activated carbon was added and the boiling solution was filtered through a Buchner funnel which contained a compacted layer of finely-divided diatomaceous silica. The cake was washed three times with 10 ml of ethanol and the hot solution together with the washings was allowed to cool to room temperature. The resulting crystals were filtered and recrystallized two more times in the same manner as described for the first crystallization. There was obtained 8.9 g of 3-(n)-butoxymethyl-5,5-diphenylhydantoin, m.p. 108°–110°. Upon testing as described above, the compound exhibited anticonvulsant activity against maximal electroshock, the $ED_{50}$ being less than 25 mg/kg. The $LD_{50}$ (oral) was also determined to be greater than 500 mg/kg.

EXAMPLE 7

5,5-Diphenylhydantoin sodium (27.5 g) was suspended in 250 ml of dimethylformamide. To the suspension was added 15 ml of chloromethylbenzylether with good stirring and the mixture was stirred at room temperature overnight. The reaction mixture was then poured into 1 liter of ice cold water and stirred for one hour. The solid product was removed by filtration and dissolved in 150 ml of hot ethanol. To the boiling solution 1 g of activated carbon was added and the hot solution was filtered through a Buchner funnel which contained a compacted layer of finely-divided diatomaceous silica. The cake was washed three times with 10 ml of ethanol and the hot solution together with the washings was allowed to cool to room temperature. The resulting crystals were filtered and recrystallized two more times in the same manner as described for the first crystallization. There was obtained 13.1 g of 3-benzyloxymethyl-5,5-diphenylhydantoin, m.p. 151°–152°.

EXAMPLE 8

Powdered phenobarbital sodium (25.4 g) was suspended at room temperature in 250 ml of dimethylformamide and 22.1 g of chloromethyldodecanyl ether was added to the suspension. The reaction mixture was stirred overnight and poured into 1 liter of ice-water; the mixture was then stirred for 3 hours and the waxy solid removed by filtration. The wet solid was dissolved in 150 ml of boiling ethanol; to the hot solution 1 g of activated carbon was added and the boiling solution was filtered through a Buchner funnel which contained a compacted layer of finely-divided diatomaceous silica. The filter cake was washed three times with 15 ml of ethanol and the hot solution together with the washings was allowed to cool overnight. The resulting crystals were filtered and recrystallized in the same manner as described for the first crystallization. There was obtained 13 g of N,N'-dilauryloxymethyl phenobarbital (also known as 1,3-dilauryloxymethyl-5-ethyl-5-phenyl barbituric acid), m.p. 48°–50°. When tested as described above the compound exhibited anticonvulsant activity against maximal electroshock, the peak activity occurring at 2 hours and the $ED_{50}$ being about 50 mg/kg. The $LD_{50}$ (oral) was determined to be greater than 500 mg/kg.

EXAMPLE 9

Sodium barbital (41.2 g.; 0.200 mole) was suspended in 200 cc of dimethylformamide in a 500 ml flask equipped with a stirrer and condenser. Chloromethyl methyl ether (32.0 g.; 0.400 mole) was added gradually over a period of 15 minutes, with stirring, to the sodium barbital slurry. The resulting mixture was stirred for four hours and then poured into 1000 ml of ice water. After stirring for an additional hour, the reaction mixture was extracted with ethyl acetate. The ethyl acetate solution was dried and the ethyl acetate was evaporated under reduced pressure to provide an oil. Purification was carried out by column chromatography using 60-200 mesh silica gel. Elution with a solvent mixture containing 1 part of ethyl acetate and 9 parts of benzene (by volume) yielded 1,3-dimethoxymethyl-5,5-diethylbarbituric acid.

Analysis calculated for $C_{12}H_{20}N_2O_5$: C, 52.93, H, 7.40; N, 10.29; Found: C, 53.07; H, 7.51; N, 10.35.

Pharmacological testing of this compound gave the following results:

Acute Toxicity
  $LD_{50}$ (oral): > 1000 mg/kg
  $LD_{50}$ (intraperitoneal): ca 1000 mg/kg
Anticonvulsant Activity
  Metrazol, $ED_{50}$: 7(4.6–8.4) mg/kg
  Time of Peak Activity: 1 hour

EXAMPLE 10

Sodium barbital (4.0 g.) was suspended in 50 ml of dimethylformamide. To the suspension was added, over a period of 5 minutes, chloromethyl n-dodecyl ether (10 g.). The suspension was heated at 110° C. for a period of 1 hour and then allowed to stand overnight without heating. The suspension was poured into 500 ml of ice water and the resulting aqueous emulsion was extracted with ethyl acetate. The ethyl acetate solution was dried and the ethyl acetate was evaporated under reduced pressure to yield an oil, which was purified by column chromatography using silica gel (70–325 mesh). Elution with benzene provided 1,3-di-n-dodecyloxymethyl-5,5-diethyl barbituric acid.

Analysis calculated for $C_{34}H_{64}N_2O_5$: C, 70.30; H, 11.11; N, 4.82; Found: C, 70.56; H, 11.17; N, 4.67.

When tested as described above, this compound exhibited anticonvulsant activity against Metrazol, the $ED_{50}$ being about 200 mg/kg; a time of peak activity of about one hour and an $LD_{50}$ (oral) of more than 1000 mg/kg.

EXAMPLE 11

Sodium secobarbital (25.5 g) was suspended in dimethylformamide (250 ml). The suspension was stirred vigorously and chloromethyl methyl ether (8.5 ml) was added over a period of 10 minutes. The reaction mixture was stirred at room temperature overnight, then poured into ice water and the oily product extracted into methylene chloride. The methylene chloride solution was dried, and the methylene chloride evaporated under reduced pressure to yield a crude oil. Purification by column chromatography using silica gel (60-200 mesh) and elution with a solvent mixture containing 1 part of ethyl acetate and 9 parts of benzene (by volume) provided 1,3-dimethoxymethyl-5-allyl-5-(2-pentyl) barbituric acid.

Analysis calculated for $C_{16}H_{26}O_5N_2$: C, 58.88; H, 8.03; N, 8.58; Found: C, 58.93; H, 8.13; N, 8.60.

Upon testing as previously described, the compound exhibited anticonvulsant activity against Metrazol, the $ED_{50}$ being about 100 mg/kg and an $LD_{50}$ (oral) of > 500 mg/kg.

EXAMPLE 12

Sodium secobarbital (25.5 g.) was dissolved in 250 ml of hot dimethylformamide. The solution was vigorously stirred and allowed to cool to room temperature to provide a fine suspension. To the suspension was added chloromethyl benzyl ether (16.5 g.) over a period of 10 minutes. The reaction mixture was stirred overnight and poured into 500 ml of ice water; the mixture was stirred for 1 hour and was extracted into methylene chloride. The methylene chloride solution was dried and the methylene chloride evaporated under reduced pressure to yield an oil. This crude oil was adsorbed on 60–200 mesh silica gel; elution with a solvent mixture containing 1 part of ethyl acetate and 20 parts of benzene (by volume) provided pure 1,3-dibenzyloxymethyl-5-allyl-5-(2-pentyl) barbituric acid.

Analysis calculated for $C_{28}H_{34}O_5N_2$: C, 70.27; H, 7.16; N, 5.85; Found: C, 70.34; H, 7.16; N, 5.67

When tested as described above, this compound exhibited anticonvulsant activity against Metrazol, the $ED_{50}$ being about 200 mg/kg and had an $LD_{50}$ (oral) of more than 1000 mg/kg.

What is claimed is:

1. A method of treating convulsions in warm-blooded animals which comprises administering to said animals an amount sufficient to produce an anticonvulsant effect of a compound having the structure

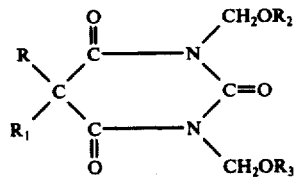

wherein R and $R_1$ are phenyl and ethyl respectively, or R and $R_1$ are individually ethyl, allyl or 2-pentyl and wherein $R_2$ and $R_3$ are individually methyl, ethyl, butyl, lauryl or benzyl.

2. A method according to claim 1 in which from about 5 to 500 mg. of said compound is administered to said warm blooded animal.

3. A method according to claim 1 in which from about 5 to 200 mg. of said compound is administered to said warm blooded animal.

4. A method according to claim 1 in which said compound is N,N'-dimethoxymethyl phenobarbital.

5. A method according to claim 1 in which said compound is N,N'-diethoxymethyl phenobarbital.

* * * * *